US007122026B2

(12) United States Patent
Rogers et al.

(10) Patent No.: US 7,122,026 B2
(45) Date of Patent: Oct. 17, 2006

(54) IMPLANTABLE INFUSION DEVICE WITH OPTIMIZED PERISTALTIC PUMP MOTOR DRIVE

(75) Inventors: Charles R. Rogers, Maple Grove, MN (US); George P. Seifert, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/125,871

(22) Filed: Apr. 22, 2002

(65) Prior Publication Data

US 2003/0199855 A1    Oct. 23, 2003

(51) Int. Cl.
*A61K 9/22* (2006.01)
(52) U.S. Cl. .................... 604/891.1; 417/44.1
(58) Field of Classification Search ............ 604/65–67, 604/118, 131, 890.1, 891.1, 30, 500, 502, 604/503, 892.1; 417/44.1, 411; 128/DIG. 12, 128/DIG. 13; 614/65–67
See application file for complete search history.

(56) References Cited

U.S. PATENT DOCUMENTS

| | | | |
|---|---|---|---|
| 4,015,419 A | 4/1977 | Morokawa et al. | |
| 4,024,447 A | 5/1977 | Epstein | |
| 4,373,527 A * | 2/1983 | Fischell | 604/891.1 |
| 4,380,722 A | 4/1983 | Oltendorf | |
| 4,381,481 A | 4/1983 | Kuppers | |
| 4,390,020 A * | 6/1983 | Herpers | 607/29 |
| 4,423,366 A | 12/1983 | Gottwald | |
| 4,426,608 A | 1/1984 | Larson et al. | |
| 4,448,197 A * | 5/1984 | Nappholz et al. | 607/29 |
| 4,510,429 A | 4/1985 | Squire | |
| 4,692,147 A | 9/1987 | Duggan | |
| 4,772,840 A | 9/1988 | Taghezout | |
| 4,831,320 A | 5/1989 | Takata | |
| 4,912,692 A | 3/1990 | Kamens | |
| 5,015,937 A | 5/1991 | Wright et al. | |
| 5,049,141 A * | 9/1991 | Olive | 604/891.1 |
| 5,105,140 A * | 4/1992 | Matthews et al. | 318/696 |
| 5,107,194 A | 4/1992 | Poehlein | |
| 5,344,431 A * | 9/1994 | Merritt et al. | 607/29 |
| 5,370,668 A * | 12/1994 | Shelton et al. | 607/29 |
| 5,402,070 A * | 3/1995 | Shelton et al. | 324/433 |

(Continued)

FOREIGN PATENT DOCUMENTS

GB     2073917 A     10/1981
WO     WO 91/10946    7/1991

*Primary Examiner*—Nicholas D. Lucchesi
*Assistant Examiner*—Matthew F. DeSanto
(74) *Attorney, Agent, or Firm*—IPLM Group, P.A.

(57) ABSTRACT

A medical device known as an implantable therapeutic substance delivery device is configured for implanting in humans to deliver a therapeutic substance such as pharmaceutical compositions, genetic materials, and biologics to treat a variety of medical conditions such as pain, spasticity, cancer, and many other conditions. The infusion device incorporates a stepper motor that controls the infusion flow rate during the service life of the device. The stepper motor is controlled by continuously varying electrical pulse parameters based on the continuously decreasing power source voltage during the service life of the substance delivery device. In particular the stepper motor electrical pulse parameters, especially duty cycle, are selected to efficiently compensate for decreasing battery voltage thereby optimizing the motor performance while maximizing the power source service life. The infusion device has a housing, a power source, a therapeutic substance reservoir, a therapeutic substance pump, and electronics. Many embodiments of the therapeutic substance delivery device with optimized pump motor drive and its methods of operation are possible.

12 Claims, 11 Drawing Sheets

U.S. PATENT DOCUMENTS

| | | | |
|---|---|---|---|
| 5,752,930 A | 5/1998 | Rise et al. | |
| 5,774,426 A | 6/1998 | Tu et al. | |
| 5,815,362 A * | 9/1998 | Kahr et al. | 361/153 |
| 6,016,448 A * | 1/2000 | Busacker et al. | 607/29 |
| 6,099,495 A | 8/2000 | Kinghorn et al. | |
| 6,108,579 A * | 8/2000 | Snell et al. | 607/29 |
| 6,154,675 A * | 11/2000 | Juran et al. | 607/29 |
| 6,167,309 A * | 12/2000 | Lyden | 607/29 |
| 6,238,367 B1 | 5/2001 | Christiansen et al. | |
| 6,264,634 B1 | 7/2001 | Yamazaki | |
| 6,740,075 B1 * | 5/2004 | Lebel et al. | 604/891.1 |
| 2003/0057899 A1 * | 3/2003 | LaCroix | 318/114 |

* cited by examiner

IMPLANTABLE INFUSION DEVICE WITH OPTIMIZED PERISTALTIC PUMP MOTOR DRIVE

RELATED APPLICATIONS

This application is related to the following co-pending applications entitled "Implantable Therapeutic Substance Infusion Device With Motor Stall Detector" by inventors Seifert et al. and "Implantable Therapeutic Substance Infusion Device With Active Longevity Projection" by inventors Rogers et al. Ser. No. 09/809,809 Filed Mar. 16, 2001, which are not admitted as prior art with respect to the present invention by its mention in this cross reference section.

FIELD OF THE INVENTION

This disclosure relates to a medical device and more particularly to an implantable therapeutic substance infusion device, also known as an implantable drug pump, optimized peristaltic pump motor drive circuit.

BACKGROUND OF THE INVENTION

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. One type of medical device is an implantable therapeutic substance infusion device.

An implantable therapeutic substance infusion device is implanted by a clinician into a patient at a location appropriate for the therapy. Typically, a therapeutic substance infusion catheter is connected to the device outlet and implanted to infuse the therapeutic substance such as a drug or infusate at a programmed infusion rate and predetermined location to treat a condition such as pain, spasticity, cancer, and other medical conditions. Many therapeutic substance infusion devices are configured so the device can be refilled with therapeutic substance through a septum while the device is implanted. Then the time the device can be implanted may not be limited by therapeutic substance stored capacity of the device. An example of an implantable therapeutic substance infusion is shown in Medtronic, Inc. product brochure entitled "SynchroMed® Infusion System" (1995).

Electrically powered implanted therapeutic substance infusion devices consume energy delivered typically by a battery, also called a power source, and can require replacement once implanted due to depletion of the battery. Typically the most significant power-consuming component in an implantable infusion device is the therapeutic substance metering motor such as a stepper motor.

A stepper motor is an electromechanical device whose rotor rotates a discrete angular amount when an electrical drive pulse is applied to the stator windings. The amplitude and the width of the electrical drive pulse must be tailored to the electromechanical properties of the motor in order to achieve rotation, stability, and optimal energy consumption. Examples of instability include the motor rotating backwards, stepping ahead then "flipping back" to its starting position, and not stepping at all. For a stepper motor to function normally and efficiently over a wide power source voltage range, the motor drive pulse needs to be adjusted proportional to the voltage change of the power source.

If all motor drive pulse parameters are held constant while the power source voltage decreases, a decrease due to normal consumption of power source energy, excess energy above that needed by the motor is delivered at the beginning of the service life of the device. This occurs because the pulse parameters needed for the end of service life, for example, pulse width, are greater than needed at the beginning.

Thus, unless the pulse parameters are appropriately varying as the power source voltage is varying, the excess energy drawn from the power source undesirably reduces the service life of the implantable pump. This may cause an early need to replace the pump which is undesirable.

Since replacement of the implanted device requires an invasive procedure of explanting the existing device and implanting a new device, it is desirable to extend battery life to the greatest extent practicable. Some previous implantable infusion devices have reduced power consumption by varying the pulse width of the motor drive signal, but stepper motors can become unstable or stall under some circumstance when the pulse width is varied from the optimal pulse width that the motor is typically designed to use. An example of a motor drive signal with a varying pulse width is shown in Japanese Patent 11,042,286 "Intracorporealy Embedded Type Liquid Medicine Supplying Apparatus" by Yamazaki (Feb. 16, 1999).

For the foregoing reasons, there is a need for an implantable therapeutic substance infusion device with optimized pump motor drive to increase the infusion device's effective service life. This increased service life reduces the overall cost of the medical therapy and the inconvenience to the patient and clinician for future device replacement surgeries.

BRIEF SUMMARY OF THE INVENTION

An implantable therapeutic substance infusion device embodiment with optimized peristaltic pump motor drive to maximize the service life of the power source while maintaining assurance that the energy needed to drive the pump motor is sufficient over the life of the power source and the life of the device. The slow continuous decrease of power source voltage versus time is periodically sampled and measured. A measurement circuit measures this voltage signal and this voltage value is used to continuously vary the motor drive parameters generated by the motor drive circuit to compensate for the decreasing voltage. The duty cycle of the short drive pulses increases as the power source voltage decreases thereby compensating for the reduced voltage drive amplitude to the motor. The electrical energy delivered by the motor drive circuit is substantially constant even when the power source voltage decreases. This invention avoids the waste of significant power source energy at the high initial power source voltage if the motor drive pulse width and repetition rate were constant over the service life of the pump and power source. The infusion device has a housing; a power source; a therapeutic substance reservoir configured for containing a therapeutic substance and being refilled with the therapeutic substance while implanted; a therapeutic substance pump fluidly coupled to the therapeutic substance reservoir, and electrically coupled to the power source; and, electronics electrically coupled to the power source and coupled to the therapeutic substance pump. The electronics include a processor; memory coupled to the processor; an infusion program residing in memory, the infusion program capable of being modified once the therapeutic substance infusion device is implanted; and, transceiver circuitry coupled to the processor for externally receiving and transmitting therapeutic substance infusion device information. Many embodiments of the therapeutic substance delivery device with optimized peristaltic pump motor drive and its methods of operation are possible.

DETAILED DESCRIPTION OF THE PREFERRED EMBODIMENTS

Figure 1:
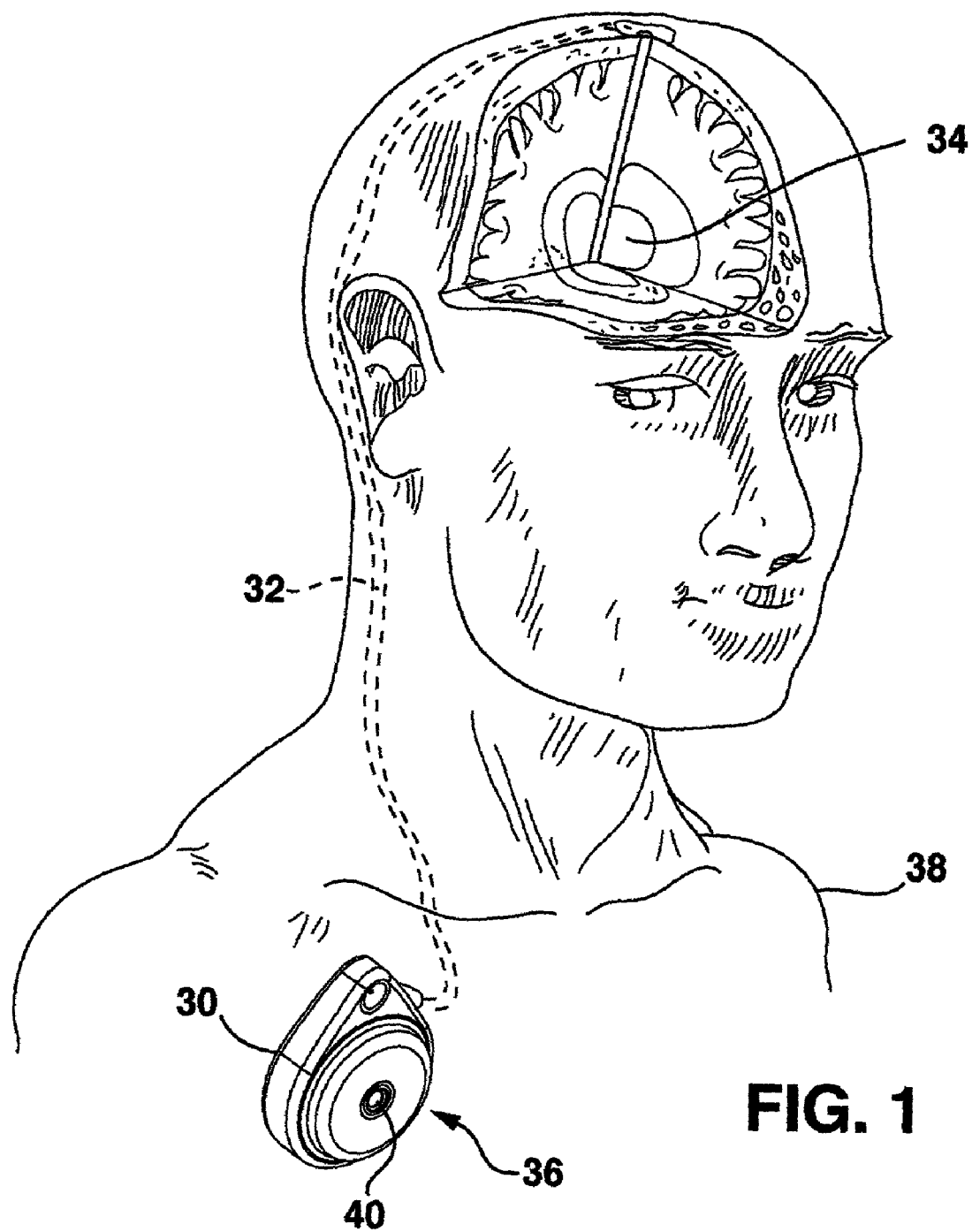
FIG. 1 shows the environment of an implantable therapeutic substance infusion device embodiment.

FIG. 1 shows the environment of an implantable medical device known as an implantable therapeutic substance delivery device 30, also known as a drug pump, having a peristaltic pump with optimized peristaltic pump motor drive embodiment. The therapeutic substance delivery device 30 operates to infuse a therapeutic substance 36 stored in therapeutic substance reservoir 44 at a programmed flow rate into a patient 38. The therapeutic substance delivery device 30 can be used for a wide variety of therapies such as pain, spasticity, cancer, and many other medical conditions.

The implantable therapeutic substance delivery device 30 is typically implanted by a surgeon in a sterile surgical procedure performed under local, regional, or general anesthesia Before implanting the therapeutic substance delivery device 30, a catheter 32 is typically implanted with the distal end position at the desired therapeutic substance delivery site 34 and the proximal end tunneled to the location where the therapeutic substance delivery device 30 is to be implanted. The implantable therapeutic substance delivery device 30 is generally implanted subcutaneous about 2.5 cm (1.0 inch) beneath the skin where there is sufficient tissue to support the implanted system. Once the therapeutic substance delivery device 30 is implanted into the patient 38, the incision can be sutured closed and the therapeutic substance delivery device 30 can begin operation.

Figure 2:
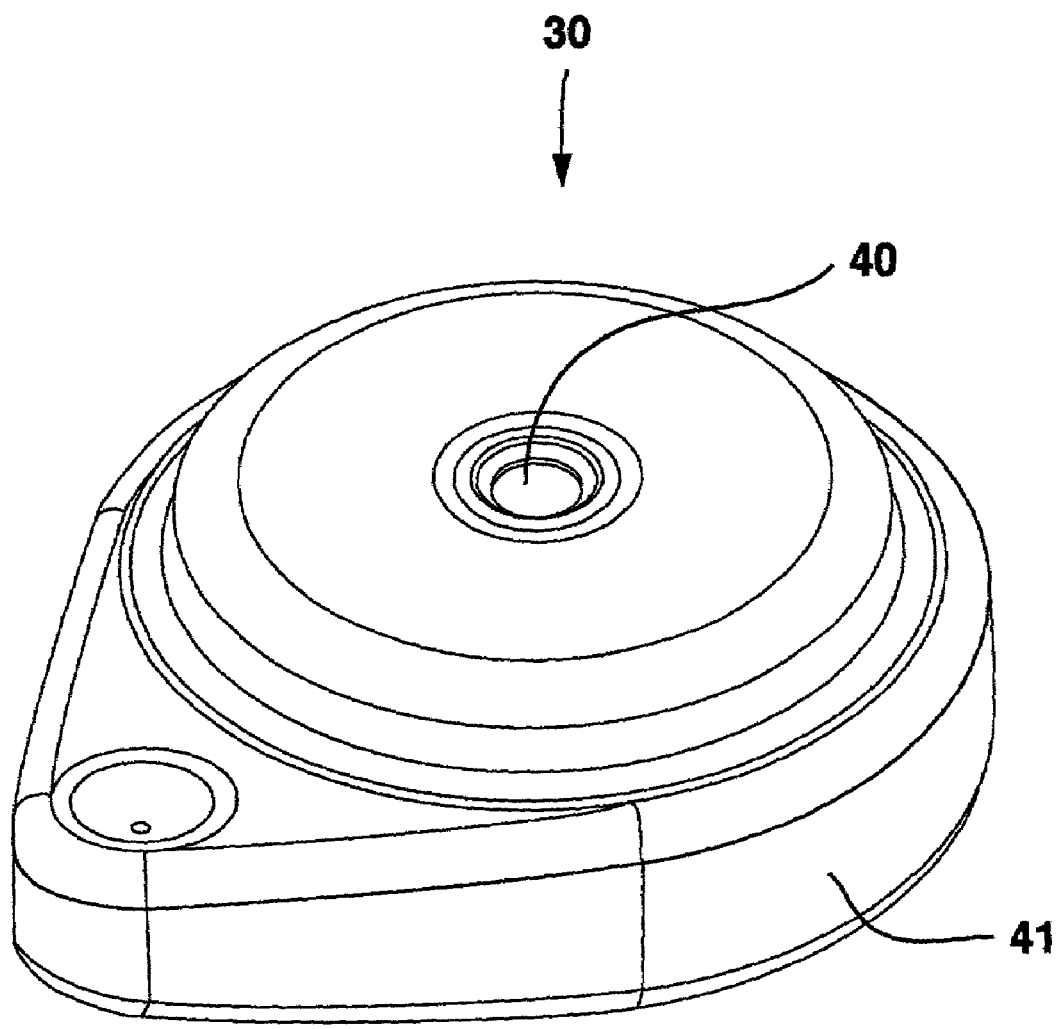
FIG. 2 shows an implantable therapeutic substance infusion device embodiment.
Figure 3:
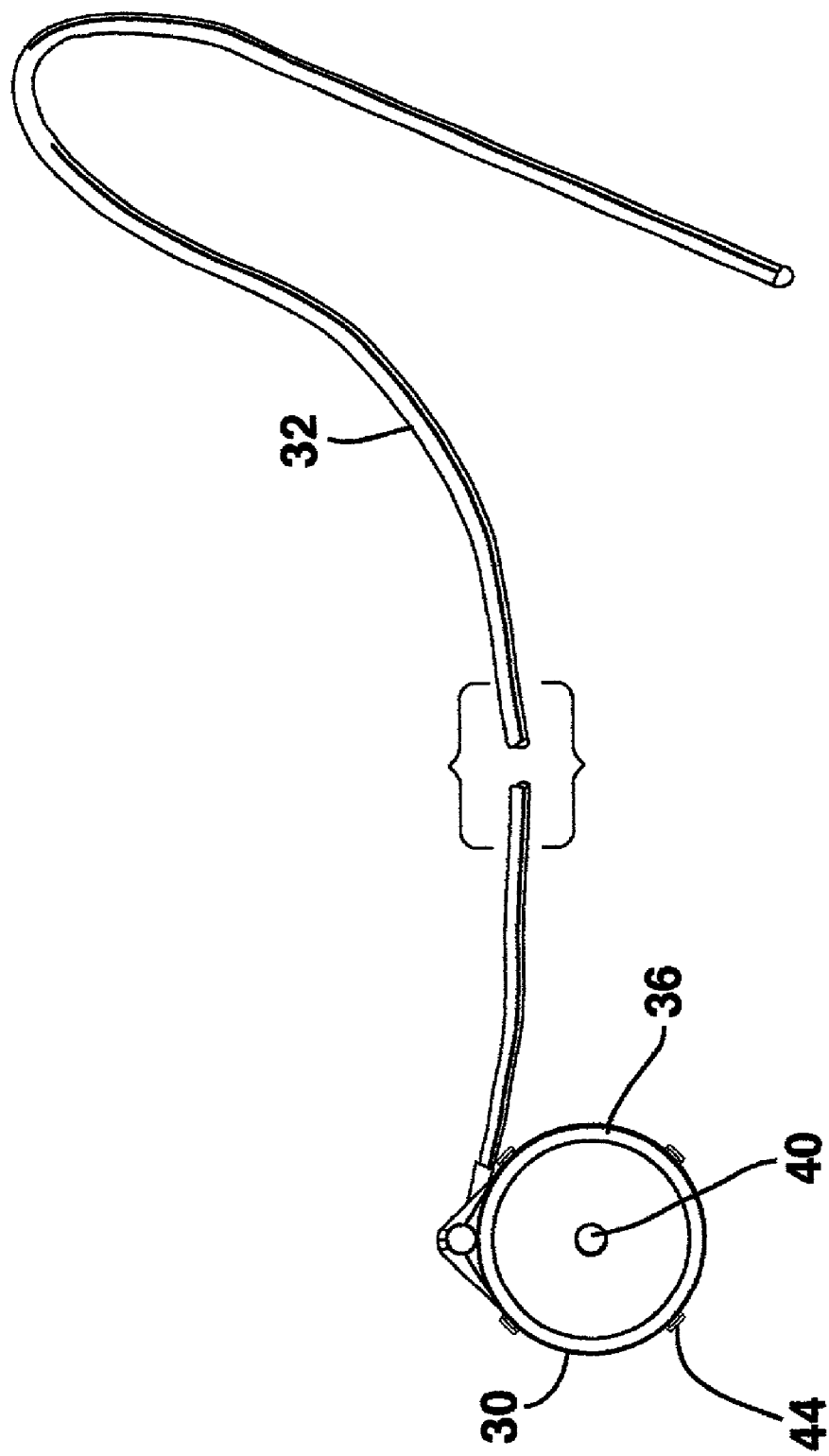
FIG. 3 shows an implantable therapeutic substance infusion device with catheter embodiment.

FIG. 2 shows an implantable therapeutic substance delivery device 30 with optimized pump motor drive embodiment with housing 41 and fill port septum 40. FIG. 3 shows implantable therapeutic substance delivery device 30 connected to catheter 32 prior to implantation into a patient 38 by a surgeon.

The therapeutic substance 36 in pump reservoir 44 inside the pump is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like.

The therapeutic substance 36 in reservoir 44 can be replenished in some embodiments of the implanted therapeutic substance delivery device 30 by inserting a non-coring needle connected to a syringe filled with therapeutic substance 36 through the patient's skin into a fill port septum 40 on the therapeutic substance delivery device 30 to fill the implanted device. The contents of the syringe are then injected into the pump reservoir 44.

If the therapeutic substance delivery device 30 requires replacement due to conditions such as power source depletion or other condition, an incision is made near the implanted therapeutic substance delivery device 30, and the old therapeutic substance delivery device 30 is removed, also known as explanted. After the old therapeutic substance delivery device 30 has been explanted, typically a new therapeutic substance delivery device 30 is then implanted.

Figure 4:
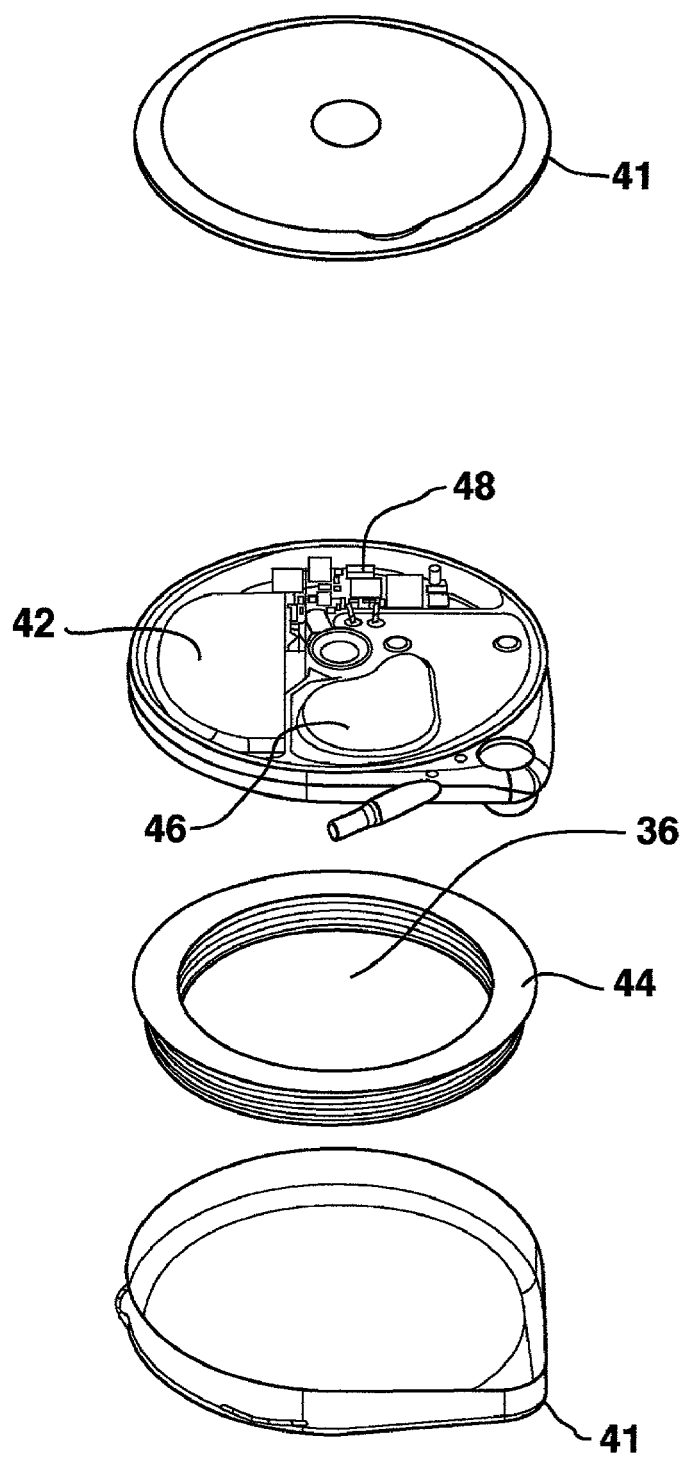
FIG. 4 shows an exploded view of an implantable therapeutic substance infusion device with peristaltic pump embodiment.

FIG. 4 shows an exploded view of an implantable therapeutic substance infusion device with optimized pump motor drive comprised of a housing 41, a power source 42, a therapeutic substance reservoir 44, a therapeutic substance pump 46, and electronics 48. The housing 41 is manufactured from a material that is biocompatible and hermetically sealed such as titanium, tantalum, stainless steel, plastic, ceramic, and the like. The power source 42 is carried in the housing 41. The power source 42, selected to operate the therapeutic substance pump 46 and electronics 48, may be a lithium ion (Li+) battery, a capacitor, and the like.

The therapeutic substance reservoir 44 is carried in the housing 41 and is configured to contain therapeutic substance 36. The therapeutic substance pump assembly 46 is carried in the housing 41, and is fluidly coupled to the therapeutic substance reservoir 44 and electrically coupled to the power source 42. The therapeutic substance pump assembly 46 is a pump sufficient for infusing therapeutic substance 36 such as the peristaltic pump with stepper motor drive that can be found in the SynchroMed® Infusion System available from Medtronic, Inc.

A stepper motor is an electromechanical device whose rotor rotates a discrete angular amount when an electrical drive pulse is applied to the stator windings. The amplitude and the width of the pulse must be tailored to the electromechanical properties of the motor in order to achieve rotation, rotational stability, and optimal energy consumption. An example is a motor that rotates 180 degrees with the application of a 3 volt, 11.2 millisecond, square pulse. A second pulse is then applied at minus 3 volts to rotate an additional 180 degrees making a complete revolution.

The stepper motor is mechanically coupled by gears to the peristaltic roller pump where the rollers rotate in such a way as to squeeze a compressible tube and drive liquid through the tube lumen in one direction. In effect the therapeutic substance 36 from the reservoir 44 flows in the tube and is metered to the patient 38 via catheter 32 to anatomical sight 34.

Examples of instability include the motor rotating backwards, stepping ahead then "flipping back" to its starting position, and not stepping at all. For a stepper motor to function normally and efficiently over a wide power source voltage range, the motor drive pulse parameters need to be adjusted proportional to the voltage change of the power source.

Figure 5:
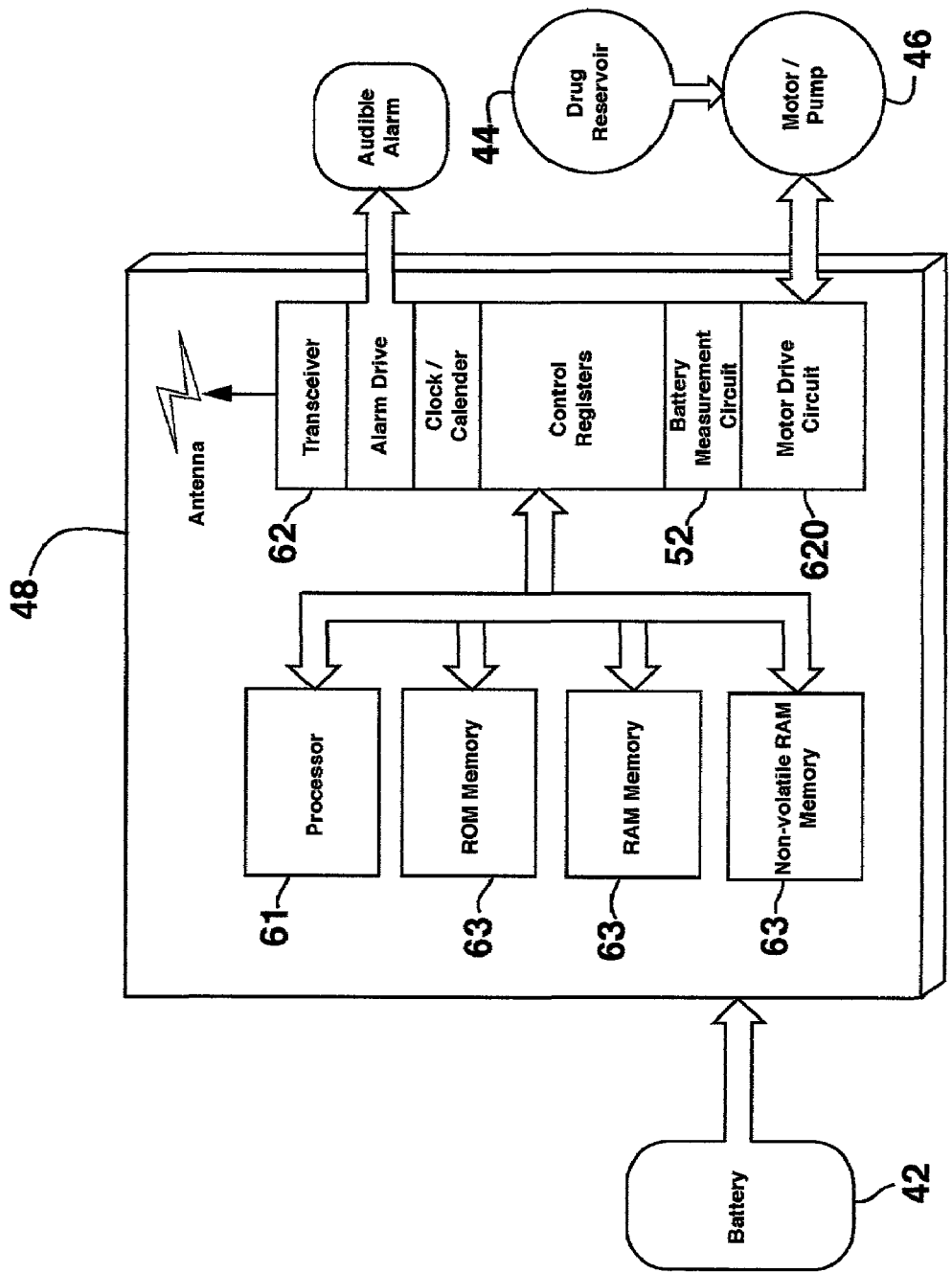
FIG. 5 shows a block diagram of an implantable therapeutic substance infusion device embodiment.

FIG. 5 shows a block diagram device embodiment. The electronics 48 are carried in the housing 41 and coupled to the therapeutic substance pump 46 and the power source 42. The electronics 48 include a processor, memory, an infusion program, and transceiver circuitry. The processor can be a microprocessor, an application specific integrated circuit (ASIC) state machine, a gate array, a controller, and the like. The electronics 48 are configured to control the therapeutic substance pump 46 infusion rate and can be configured to operate many other features such as patient alarms and the like. The infusion program and other device parameters and patient information reside in memory and are capable of being modified once the therapeutic substance infusion device is implanted. The transceiver circuitry is coupled to the processor for externally receiving and transmitting therapeutic substance infusion device information.

Figure 6:
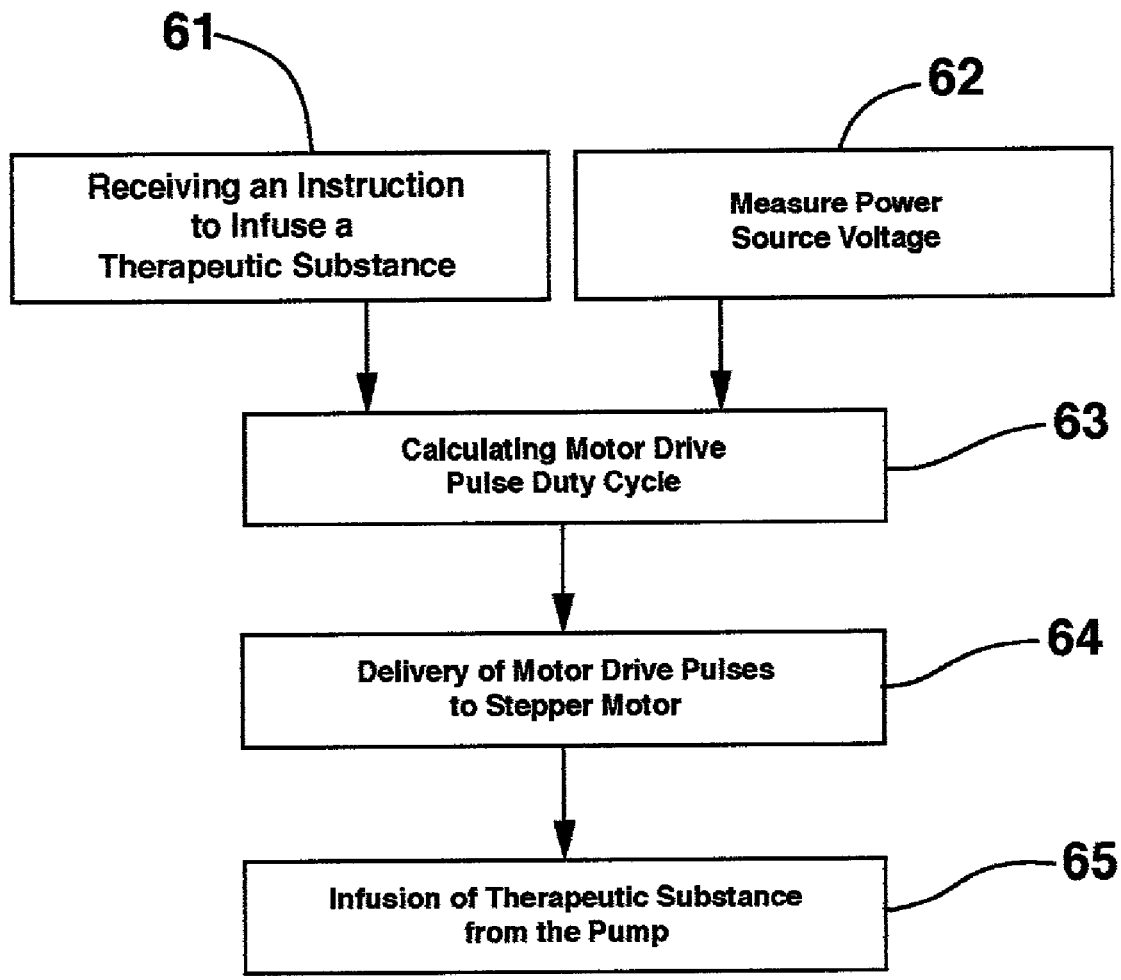
FIG. 6 shows flow diagram for the motor drive control embodiment.

FIG. 6 shows a flow chart of a method for operating a therapeutic substance infusion device 30 with optimized pump motor drive. The method embodiment includes receiving an instruction to infuse a therapeutic substance 61. Together with the elements of measuring, receiving and storing the power source voltage signal in 62, the drive pulse duty cycle is calculated or provided by a look-up table in 63. The drive pulse duty cycle is used for delivery of motor drive pulses 64 to the motor that generates the infusion of therapeutic substance from the pump 65.

Figure 7:
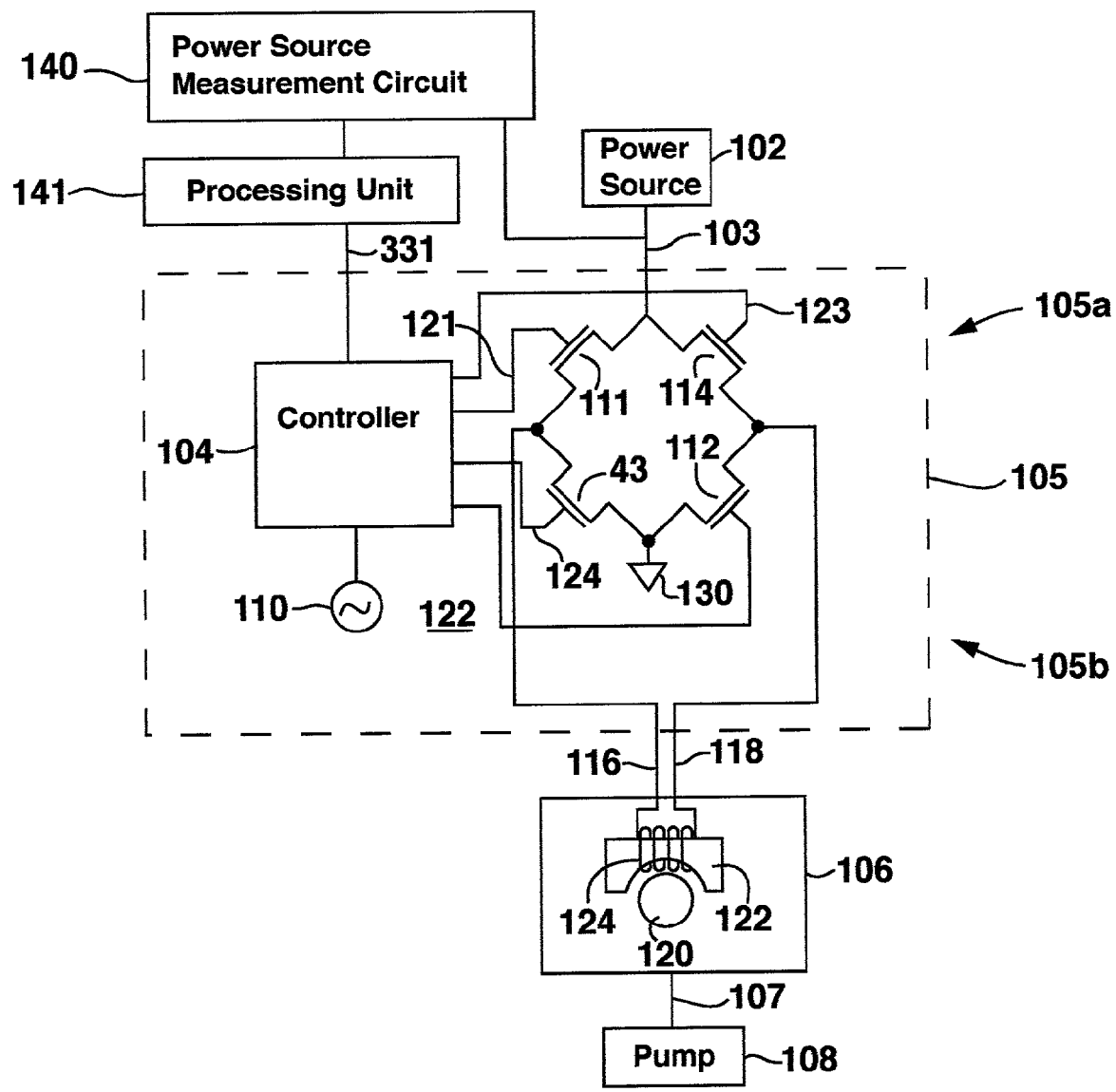
FIG. 7 shows a schematic diagram of stepper motor control system embodiment.

FIG. 7 shows a schematic diagram of stepper motor control system to illustrate the components of the preferred embodiment. The stepper motor 106 is connected to the power source 102 via the motor drive circuit 105, and mechanically coupled with gears 107 to the therapeutic substance infusion pump 108. The motor drive circuit 105 is configured with a drive interval timing circuit 105a and a drive pulse circuit 105b. The drive interval timing circuit 105a specifies a substantially fixed drive interval for drive energy to be delivered to the motor 106 to operate a therapeutic substance pump 108 according to a therapy program. The drive pulse circuit 105b is coupled to the power source measurement circuit 140 to generate a predetermined number of drive pulses within the drive interval according to the power supply 102 voltage to reduce motor 106 energy consumption. The duty cycle of short drive pulses varies according to the power source voltage 95 of FIG. 9 at terminal 103 as measured by the power source measurement circuit 140 to reduce motor energy consumption.

Figure 8:
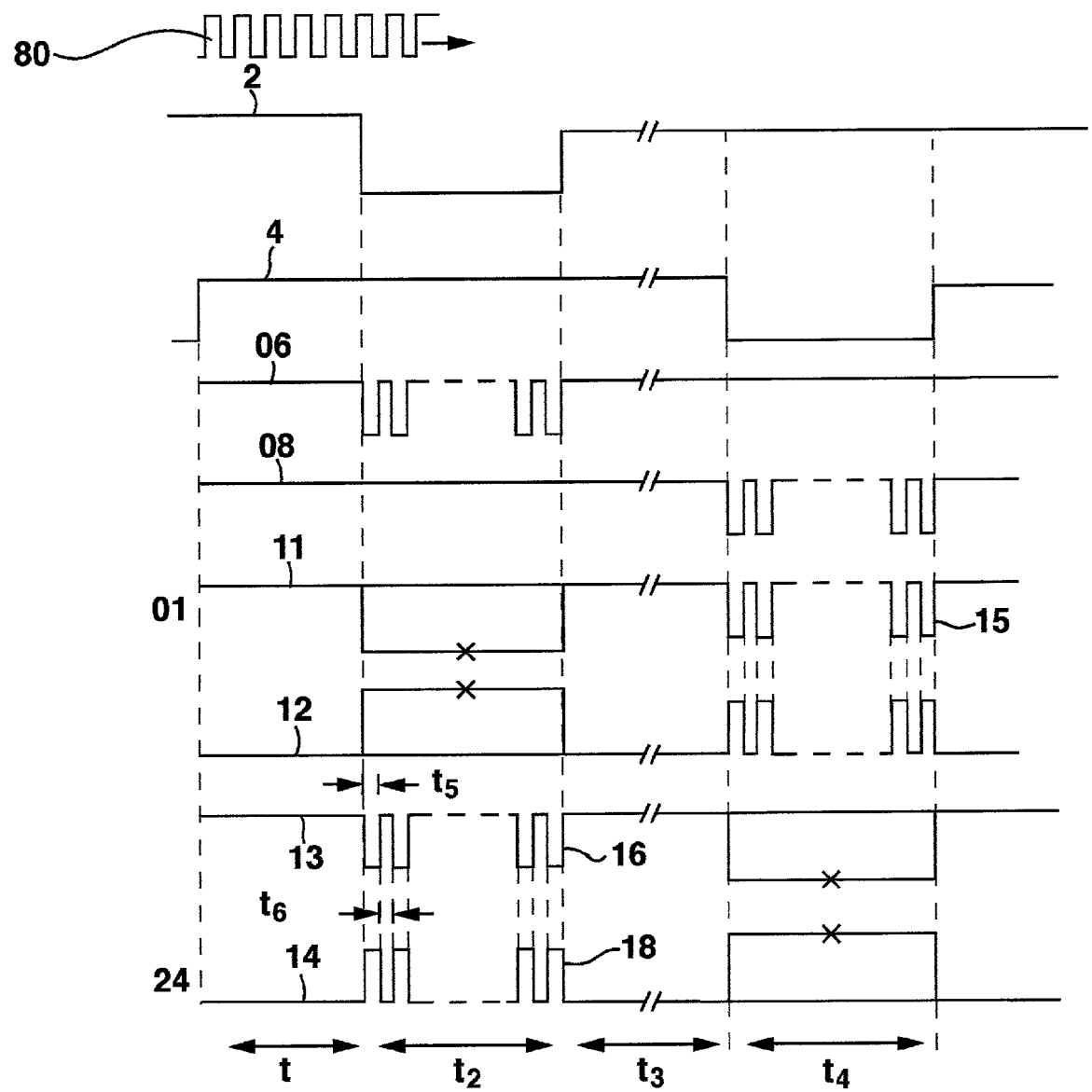
FIG. 8 shows an electrical pulse diagram versus time for the chopper motor control embodiment.

FIG. 8 shows the repetition rate of the long fixed drive period t2 varies dependent on the programmed pump flow rate in accordance with the therapy program. For example, the repetition rate is high for high therapy flow rates, and the repetition rate is low for low therapy flow rates.

In FIG. 7 the power source voltage 95 at terminal 103 is feed to the quad switches 111, 112, 113, and 114 as well the power source measurement circuit 140. The power source measurement circuit 140 is composed of a standard analog-to-digital converter as well as other electrical components. The power source measurement circuit 140 generates a signal or digital word proportional to the power source voltage that is fed to the processing unit 141. The processing unit 141 produces a duty cycle control signal or digital word that is fed to the controller 104 in the motor drive circuit 105. The controller 104 in the motor drive circuit is composed of standard digital logic, registers and other logic components to configure the motor drive pulses. Registers may include but are not limited to a pulse interval register, a drive pulse width register, a drive pulse duty cycle register, and a drive pulse expiration register.

The controller 104 outputs electrical pulses to drive the four motor drive switches 111, 112, 113, and 114. Outputs 116 and 118 of the quad switch assembly produce a motor drive pulse train that energizes the motor stator magnet 122, in turn rotating the motor rotor 120. The motor stator coil 124 is wound around the magnetic material stator 122. The rotor 120 is mechanically coupled by gears 107 to the pump mechanism 108. The rotor 120 of the stepper motor rotates in such a way as to propel and meter the therapeutic infusion substance 36 from the pump 30 to the patient 38.

This invention achieves motor drive energy optimization by dividing the usual long drive pulse into numerous shorter pulses. For example, the long single drive pulse can be performed by 23 shorter pulses applied over the time period t2 in FIG. 8. Due to the large inductance of the motor's stator winding 124, the flow of current is not significantly disrupted at each short pulse. The duty cycle, ratio of "on time" to "total time", of the short pulses is directly proportional to the energy savings compared to a 100% "on time" drive pulse. The duty cycle changes in small discrete increments over the usable power source voltage range such that the energy that drives the motor is substantially constant and of proper amplitude for stable motor function. For example, the duty cycle increases in $\frac{1}{16}$ steps as the power source voltage decreases and vice versa.

FIG. 8 illustrates how the stepper motor pulse duty cycle is achieved. The long pulse t2 is combined or commutated with chopper oscillator pulses 80 from chopper oscillator 110 in the controller 104 of the motor drive circuit 105. The long motor drive pulse width t2 is fixed at 11.2 milliseconds. The 2048 hertz chopper oscillator 110 provides square wave pulses 80 that are used to achieve the short drive pulse t5. The duty cycle of the 2048 hertz pulses t5 in periods t2 and t4 are dependent on the power source voltage as described above. The predetermined number of short drive pulses t5 are about 23 pulses within the substantially fixed drive interval of 11.2 milliseconds of t2 and t4. The drive periods t2 and t4 have a duty cycle in the range from about 75% to about 100%. This combination of varying short pulse parameters achieves substantially constant motor drive energy to reliably operate a therapeutic substance pump according to a therapy program.

Figure 9:
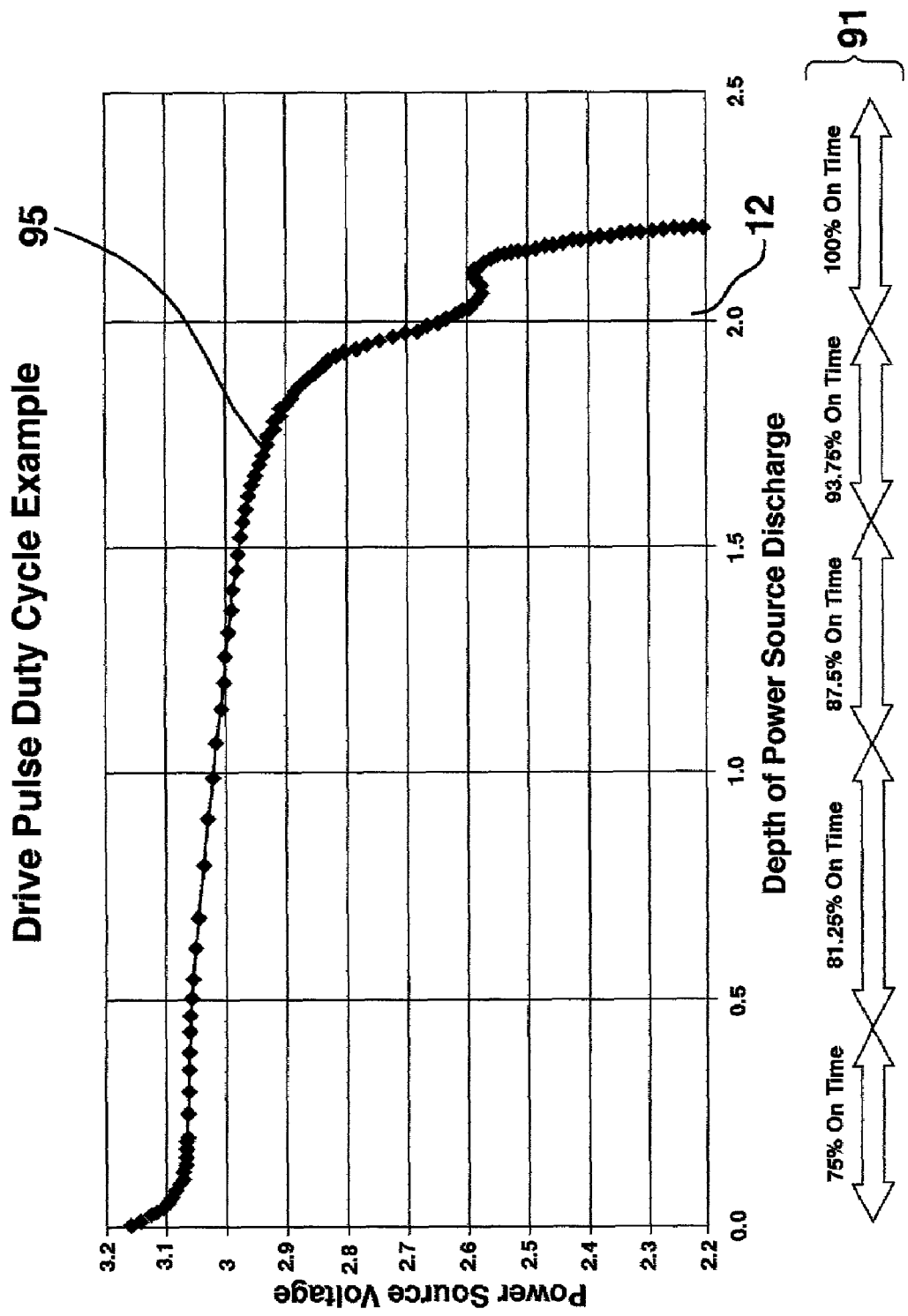
FIG. 9 shows a diagram of the power source voltage versus depth of discharge of the power source superimposed with drive pulse duty cycle embodiment.

FIG. 9 illustrates the continuously varying power source voltage 95 versus the Depth of Power Source Discharge during the service life of the infusion device. Superimposed on FIG. 9 is the motor drive short pulse duty cycle 91 expressed in percent. As the power source voltage decreases, the duty cycle increases, ranging from 75% to 100%. The end of service life 92 of the power source 42 is where 100% duty cycle occurs. Until the end of service life is reached, the duty cycle of the stepper motor varies to compensate for the decreasing power source voltage.

Figure 10:
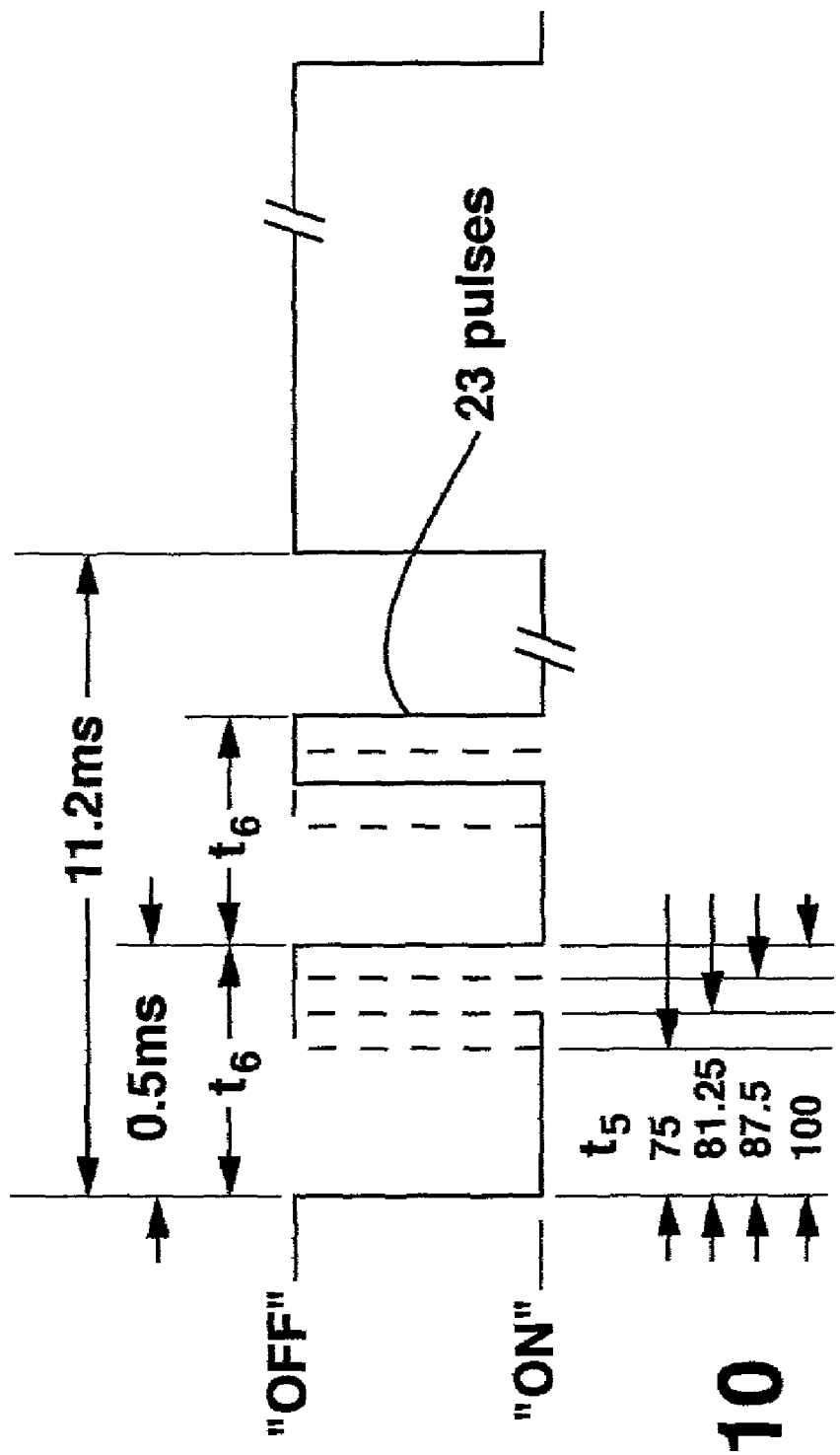
FIG. 10 shows the drive pulse duty cycle with varying duty cycles embodiment.

FIG. 10 illustrates the duty cycle, defined as t5 divided by t6, as it varies depending on power source voltage 95. At 100% duty cycle, the short drive pulses t5 are on during the entire 11.2 millisecond drive period t2 in FIG. 8. At 75% duty cycle, the long drive pulse is composed of 23 consecutive short drive pulses each at about 0.75/2048 hertz=0.366 milliseconds long.

Figure 11:
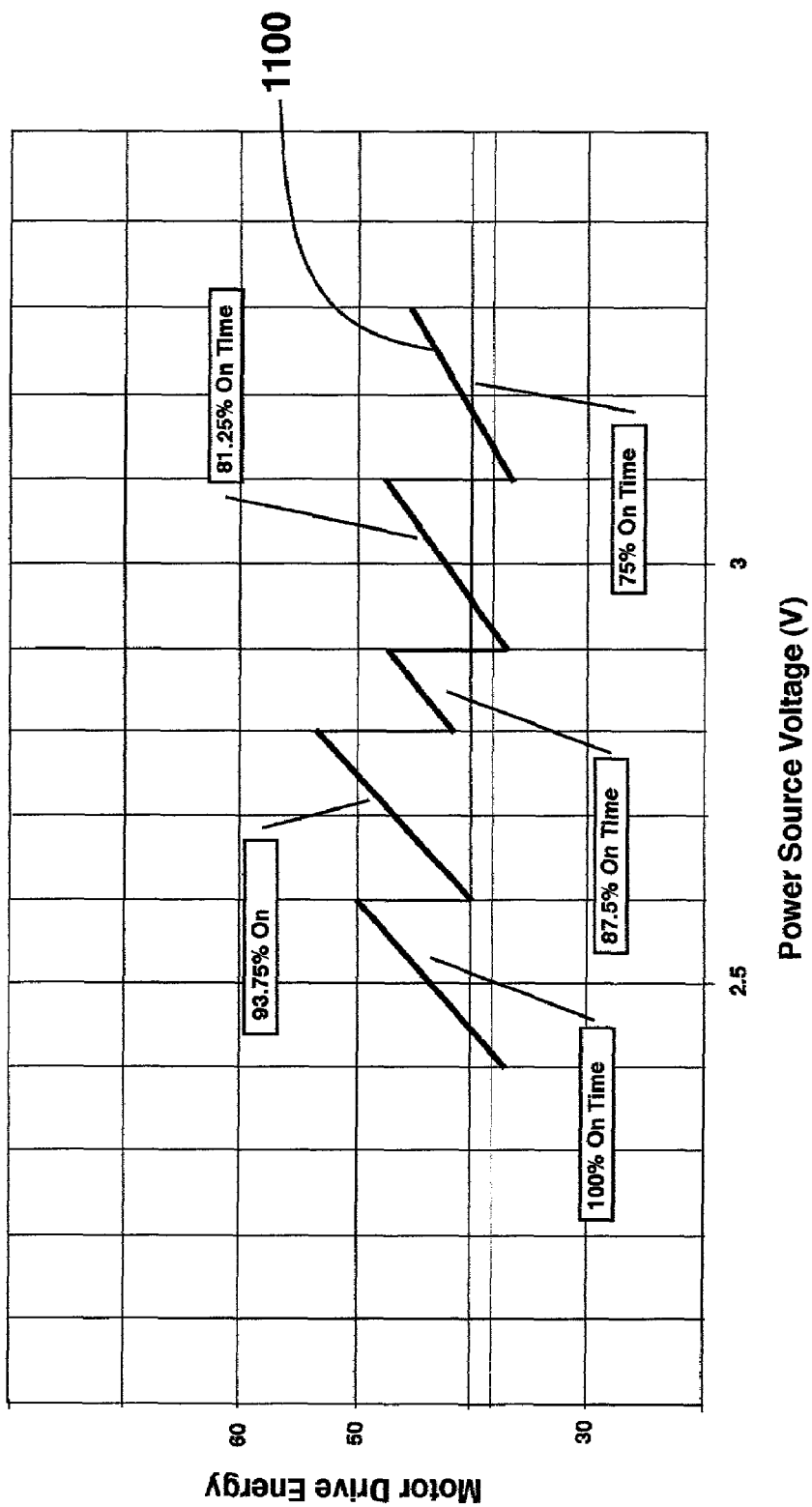
FIG. 11 shows that the motor drive pulse energy is substantial constant over the useful voltage range of the power source embodiment.

FIG. 11 illustrates the long pulse motor drive energy 1100 is substantially constant versus power source voltage. This near constant delivered energy assures stable and reliable motor 120 rotation even when the power source voltage 95 decreases.

Many other related functions could be derived from this optimized motor drive invention. For example, if a motor stall is detected, the drive pulse duty cycle could be increased or decreased to overcome the motor stall or to do diagnostics of the stall. An intermittent motor stall might occur due to significant environmental magnetic field interactions such as experienced with magnetic resonance imaging technology.

In addition, if a very large change of power source current is needed, the resultant anticipated power source voltage reduction could be predicted using a power source forecast circuit. The power source forecast circuit identifies that the power source voltage will change abruptly and that the duty cycle must be adjusted. Typically the duty cycle is increased in anticipation of lower power source voltage. Such a dynamic prediction may be needed because of inherent time delays of the power source measuring or processing system. Large power source current changes might occur when the pump infusion rate is abruptly changed from a very low rate to a very high rate or an alarm is activated.

Thus, the implantable therapeutic substance infusion device 30 embodiments with optimized pump motor drive achieves the maximum service life of the power source while maintaining assurance that the stepper motor will function normally over the entire range of power source voltages. An energy efficient motor drive is achieved based on measuring power source voltage and continuously controlling the motor drive pulse parameters to minimize the electrical energy delivered to the pump motor. A predetermined number of drive pulses is selected to operate the stepper motor while substantially maintaining motor stability and avoid motor stall.

Thus, embodiments of the implantable infusion device with optimized peristaltic pump motor drive are disclosed to increase the infusion devices effective service life. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable infusion device with energy efficient motor drive, comprising:
    a housing;
    a power source carried in the housing;
    a therapeutic substance reservoir carried in the housing, the therapeutic substance reservoir configured for containing a therapeutic substance and being refilled with the therapeutic substance while implanted;
    a therapeutic substance pump carried in the housing, the therapeutic substance pump fluidly coupled to the therapeutic substance reservoir, and electrically coupled to the power source;
    a motor coupled to the power source and coupled to the therapeutic substance pump; electronics carried in the housing, the electronics coupled to the motor and the power source, the electronics including,
        a processor,
        memory coupled to the processor,
        an infusion program residing in memory, the infusion program capable of being modified once the therapeutic substance infusion device is implanted;
        transceiver circuitry coupled to the processor for externally receiving and transmitting therapeutic substance infusion device information; a power source measurement circuit to measure power source voltage; and,
    a motor drive circuit configured to generate a varying duty cycle of drive pulses in a substantially fixed drive interval, the varying duty cycle of drive pulses increasing as the power source voltage measured by the power source measurement circuit to decreases to optimize and reduce motor energy consumption.

2. The implantable infusion device as in claim 1 wherein the motor drive circuit uses logic contained in registers to configure the drive pulses.

3. The iniplantable infusion device as in claim 2 wherein registers include a pulse interval register, a drive pulse width register, a drive pulse duty cycle register, and a drive pulse expiration register.

4. The implantable infusion device as in claim 1 wherein the drive interval has a duty cycle in the range from about 75% to about 100% of a step interval.

5. The inaplantable infusion device as in claim 1 further comprising a power source forecast circuit or program that identifies that the power source voltage will change abruptly and that the drive duty cycle must be adjusted.

6. An implantable infusion device with energy efficient motor drive, comprising:
    a housing;
    a power source carried in the housing;
    a therapeutic substance reservoir carried in the housing, the therapeutic substance reservoir configured for containing a therapeutic substance and being refilled with the therapeutic substance while implanted;
    a therapeutic substance pump carried in the housing, the therapeutic substance pump fluidly coupled to the therapeutic substance reservoir, and electrically coupled to the power source;
    a motor coupled to the power source and coupled to the therapeutic substance pump; electronics carried in the housing, the electronics coupled to the motor and the power source, the electronics including,
        a processor,
        memory coupled to the processor,
        an infusion program residing in memory, the infusion program capable of being modified once the therapeutic substance infusion device is implanted;
        transceiver circuitry coupled to the processor for externally receiving and
        transmitting therapeutic substance infusion device information; a power source measurement circuit to measure power source voltage; and,
    a motor drive circuit configured to generate a varying duty cycle of drive pulses in a substantially fixed drive interval, the varying duty cycle of drive pulses varying according to the power source voltage measured by the power source measurement circuit to optimize and reduce motor energy consumption; wherein the motor drive circuit comprises,
- a drive interval timing circuit that specifies a substantially fixed drive interval for drive energy to be delivered to the motor to operate a therapeutic substance pump according to a therapy program; and,
- a drive pulse circuit coupled to the power source measurement circuit that generates a predetermined number of drive pulses within the drive interval according to the power supply voltage to reduce motor energy consumption.

7. The implantable infusion device as in claim 6 wherein the motor drive circuit uses logic contained in registers to configure the drive pulses.

8. The implantable infusion device as in claim 7 wherein registers include a pulse interval register, a drive pulse width register, a drive pulse duty cycle register, and a drive pulse expiration register.

9. The iniplantable infusion device as in claim 6 wherein the predetermined number of drive pulses are in the range from about 10 to about 25 drive pulses within the substantially fixed drive interval.

10. The implantable infusion device as in claim 6 wherein the drive interval has a duty cycle in the range from about 75% to about 100% of a step interval.

11. The implantable infusion device as in claim 6 wherein the predetermined number of drive pulses is selected to operate the stepper motor while substantially maintaining motor stability and substantially avoid motor stall.

12. The implantable infusion device as in claim 6 further comprising a power source forecast circuit or program that identifies that the power source voltage will change abruptly and that the drive duty cycle must be adjusted.

\* \* \* \* \*